(12) United States Patent
Sakal et al.

(10) Patent No.: US 7,449,153 B2
(45) Date of Patent: Nov. 11, 2008

(54) TRAY FOR SLIDE PROCESSING

(75) Inventors: Robert Sakal, Bolton, MA (US); Kevin Patenaude, Lowell, MA (US); Mark Girardi, North Andover, MA (US)

(73) Assignee: Cytyc Corporation, Marlborough, MA (US)

( * ) Notice: Subject to any disclaimer, the term of this patent is extended or adjusted under 35 U.S.C. 154(b) by 62 days.

(21) Appl. No.: 11/459,306

(22) Filed: Jul. 21, 2006

(65) Prior Publication Data

US 2008/0019880 A1 Jan. 24, 2008

(51) Int. Cl.
*G01N 35/00* (2006.01)
*B01L 9/00* (2006.01)
*B01L 9/06* (2006.01)

(52) U.S. Cl. ......................... 422/104; 422/99
(58) Field of Classification Search .................. 422/99, 422/104
See application file for complete search history.

(56) References Cited

U.S. PATENT DOCUMENTS

| | | |
|---|---|---|
| 5,143,627 A | 9/1992 | Lapidus et al. |
| 5,282,978 A | 2/1994 | Polk, Jr. et al. |
| 5,439,649 A * | 8/1995 | Tseung et al. .................. 422/99 |
| 6,066,300 A * | 5/2000 | Carey et al. ................. 422/104 |
| 6,309,362 B1 | 10/2001 | Guirguis |
| 6,562,299 B1 | 5/2003 | Ostgaard et al. |
| 2003/0207455 A1 | 11/2003 | Ostgaard et al. |
| 2003/0207456 A1 | 11/2003 | Ostgaard et al. |
| 2005/0161414 A1 | 7/2005 | Wescott |

FOREIGN PATENT DOCUMENTS

| | | |
|---|---|---|
| EP | 0802413 | 10/1997 |
| JP | 60237368 | 11/1985 |
| WO | 0151909 | 7/2001 |
| WO | 2005115620 | 12/2005 |

OTHER PUBLICATIONS

PCT International Search Report for PCT/US2007/073260, Applicant CYTYC Corp., Forms PCT/ISA/210 and 220, dated Dec. 5, 2007 (6 pages).
PCT Written Opinion of the International Search Authority for PCT/US2007/073260, Applicant CYTYC Corp., Form PCT/ISA/237, dated Dec. 5, 2007 (8 pages).

* cited by examiner

*Primary Examiner*—Walter D. Griffin
*Assistant Examiner*—Christine T Mui
(74) *Attorney, Agent, or Firm*—Vista IP Law Group LLP

(57) ABSTRACT

A carrier for slide processing comprises a plurality of first locations, each configured to hold a vial containing a biological sample, and a corresponding plurality of second locations, each configured to hold a slide.

9 Claims, 2 Drawing Sheets

TRAY FOR SLIDE PROCESSING

FIELD OF THE INVENTION

The present invention is in the field of automated processing of biological slides. In particular, the present invention is in the field of trays used for holding the biological sample and the slide.

BACKGROUND

Several automated sample processors are known in the art for the preparation of slides with cells taken from biological specimen. For example, U.S. Pat. Nos. 5,143,627, 5,282,978, and 6,562,299, and U.S. Patent Application Publication Nos. 2003-0207455 A1 and 2003-0207456 A1 describe several of such automated systems.

In certain automated systems, such as the ThinPrep® TP2000 (Cytyc Corp.), the user manually feeds the slides and the vials containing the biological sample to the processor. Once the cells are smeared on the slide, a one-to-one relationship between the sample vial and the microscope slide is established, which needs to be maintained until the slide is reviewed by a medical expert. This one-to-one relationship is often referred to as the "chain of custody."

In addition to marking the slide with the same identifier, such as the patient name or number, that appears on the vial, users regularly keep each vial in close proximity to its corresponding slide. Normally, this is accomplished by placing a blank slide on top of each vial while the vials are lined up to be processed by the processor. After the slides are smeared, the slides are again kept laying on top of their corresponding vials. This process creates opportunities for mistakes and accidents to create a mix-up. Therefore, a need exists in the art for a container that keeps the vials and their corresponding slides in close proximity to each other.

SUMMARY OF THE INVENTION

Disclosed herein is a carrier for slide processing, comprising a plurality of locations each configured to hold a vial, where the is vial is configured to hold a biological sample; and a plurality of locations each configured to hold a slide; where there are as many of the slide locations as there are vial locations. Also disclosed are methods of using the carrier with an automated sample processor.

Other and further embodiments and features thereof will be apparent from the following detailed description, taken in conjunction with the drawings

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below. It is, however, expressly noted that the present invention is not limited to these embodiments, which are provided by way of example and not limitation.

The carriers disclosed herein are best suited for use with ThinPrep® TP2000 (Cytyc Corp.) or ThinPrep® TP3000 (Cytyc Corp.). However, the carriers disclosed herein can be used with any of the processors currently on the market or later developed. The carriers of the illustrated embodiments provide for retaining the unique relationship between a sample vial and a prepared slide, while minimizing the chance for separation of the slide from its corresponding vial or creating confusion or doubt as to the correct relationship.

Thus, in the first aspect, the present invention relates to a carrier for slide processing, comprising a location configured to hold a vial and a location configured to hold a slide; and a location configured to hold a filter.

Figure 1:
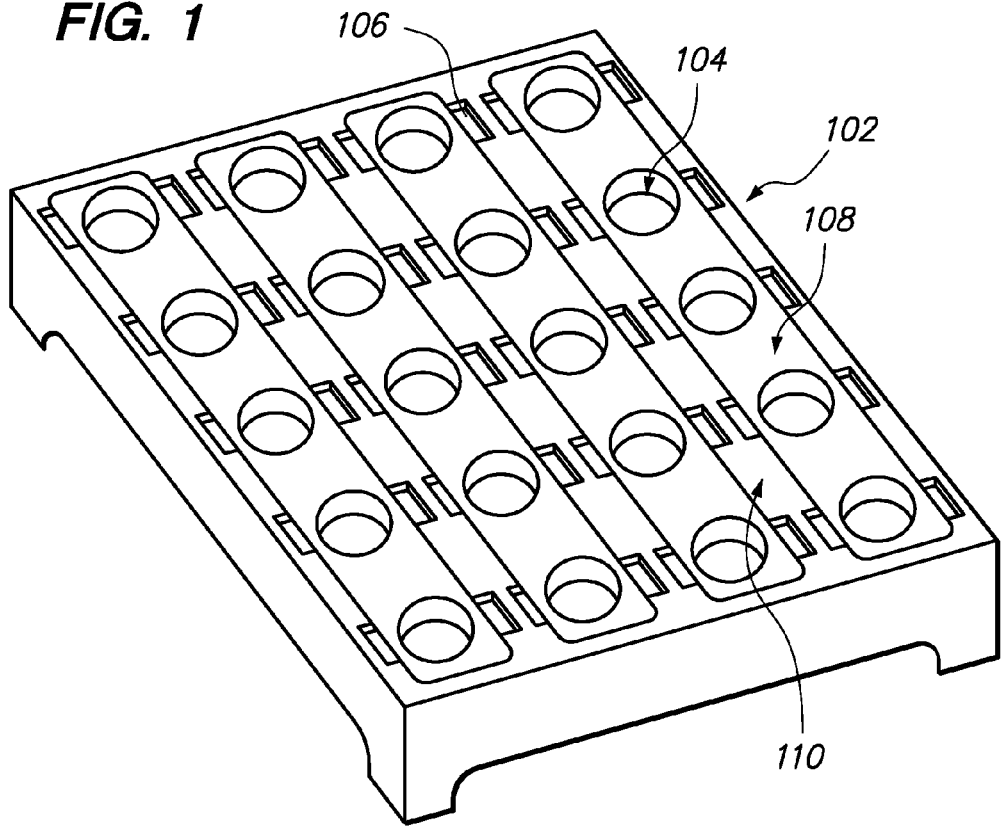
FIG. 1 depicts one embodiment of the carrier of the present invention, having slide locations superimposed on vial locations.

FIG. 1 depicts one embodiment of the carrier disclosed herein. The carrier 102 comprises a plurality of locations 104 each configured to hold a vial. Each location 104 can be a hole in the carrier 102. The hole 104 can have a solid bottom, or the bottom can be open. The carrier 102 also comprises a plurality of locations 106 each configured a microscope slide. The slide can be a glass slide or a plastic slide. In some embodiments, the slide is a conventional slide used for preparing biological samples and viewing them through a microscope.

In some of these embodiments, the carrier 102 comprises a plurality of troughs 108, each separated from another by a wall 110. Thus, the top surface of each trough 108 is lower than the top surface of each wall 110. In some embodiments, all troughs 108 have the same height. In further embodiments, all walls 110 have the same height. Vial locations 104 are located in the troughs 108. Slide locations 106 are configured on walls 110 such that when a slide is placed in a location 106, the slide bridges a trough 108 from one wall 110 to another wall 110.

In some embodiments, such as the one shown in FIG. 1, each location 106 is superimposed over one location 104. Thus, when a vial is placed in a location 104, a microscope slide is placed in a location 106 such that the microscope slide is located directly above the vial. This juxtaposition of the microscope slide and the vial provides a one-to-one relationship between the microscope slide and the vial and minimizes confusion and mix-ups.

In some embodiments, the carrier 102 is configured to hold an even number of vials, with a corresponding even number of slides. In other embodiments, the carrier 102 is configured to hold an odd number of vials, with a corresponding odd number of slides. In further embodiments, the carrier 102 is configured to hold at least 5 vials. In other embodiments, the carrier 102 is configured to hold at least 10 vials. In yet other embodiments, the carrier 102 is configured to hold at least 15 vials. In other embodiments, the carrier 102 is configured to hold at least 20 vials. In some embodiments, such as the one shown in FIGS. 1 and 2, the carrier 102 is configured to hold 20 vials.

In some embodiments, the carrier 102 is configured to have as many slide locations as there are vial locations.

Figure 2:
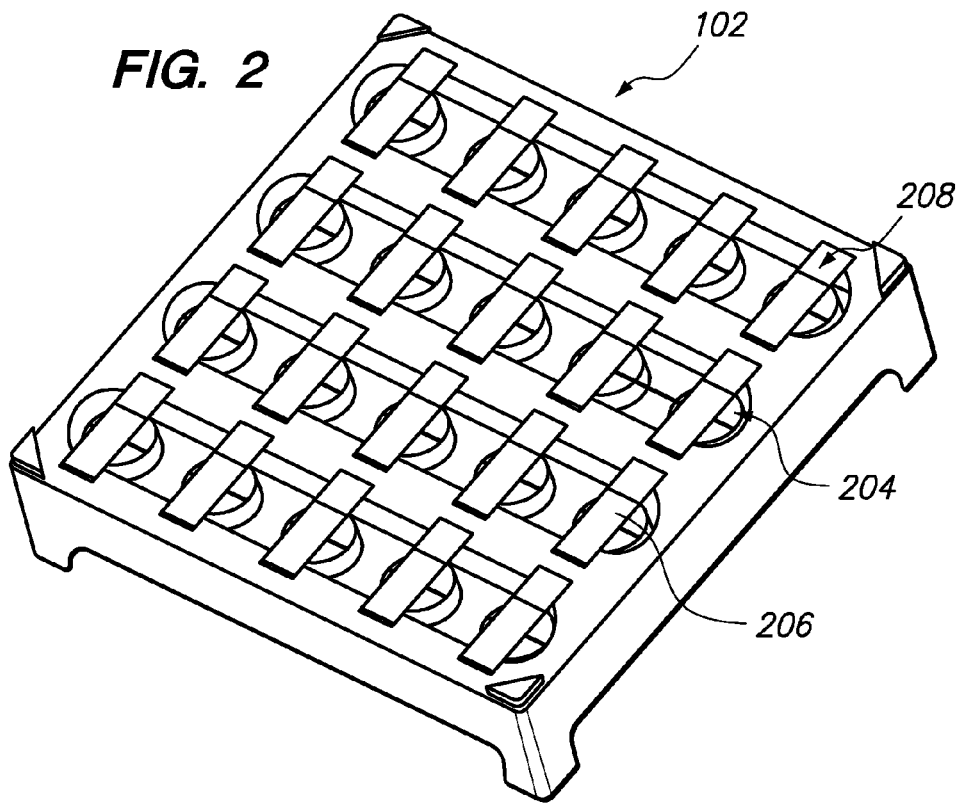
FIG. 2 depicts the embodiment of the carrier of the present invention, where slide locations are superimposed to vial locations, showing the vials and slides in their respective locations.

FIG. 2 shows an embodiment of the carrier disclosed herein, showing the microscope slides 206 and the vials 204 placed in their respective locations. Each slide 206 can have a location 208 for a label. Preferably, the label contains at least one identifier, which is the same as an identifier on a label on the vial. The identifier can be the name of a patient, an identifying medical record number associated with a patient, and the like.

While FIGS. 1 and 2 show one configuration of the locations 104 and 106 within the carrier 102, those of skill in the art recognize that other configurations of these locations are possible. Embodiments of the present invention are not limited to the configurations shown in FIGS. 1 and 2, and include all manner of placing these locations on the carrier 102.

Figure 3:
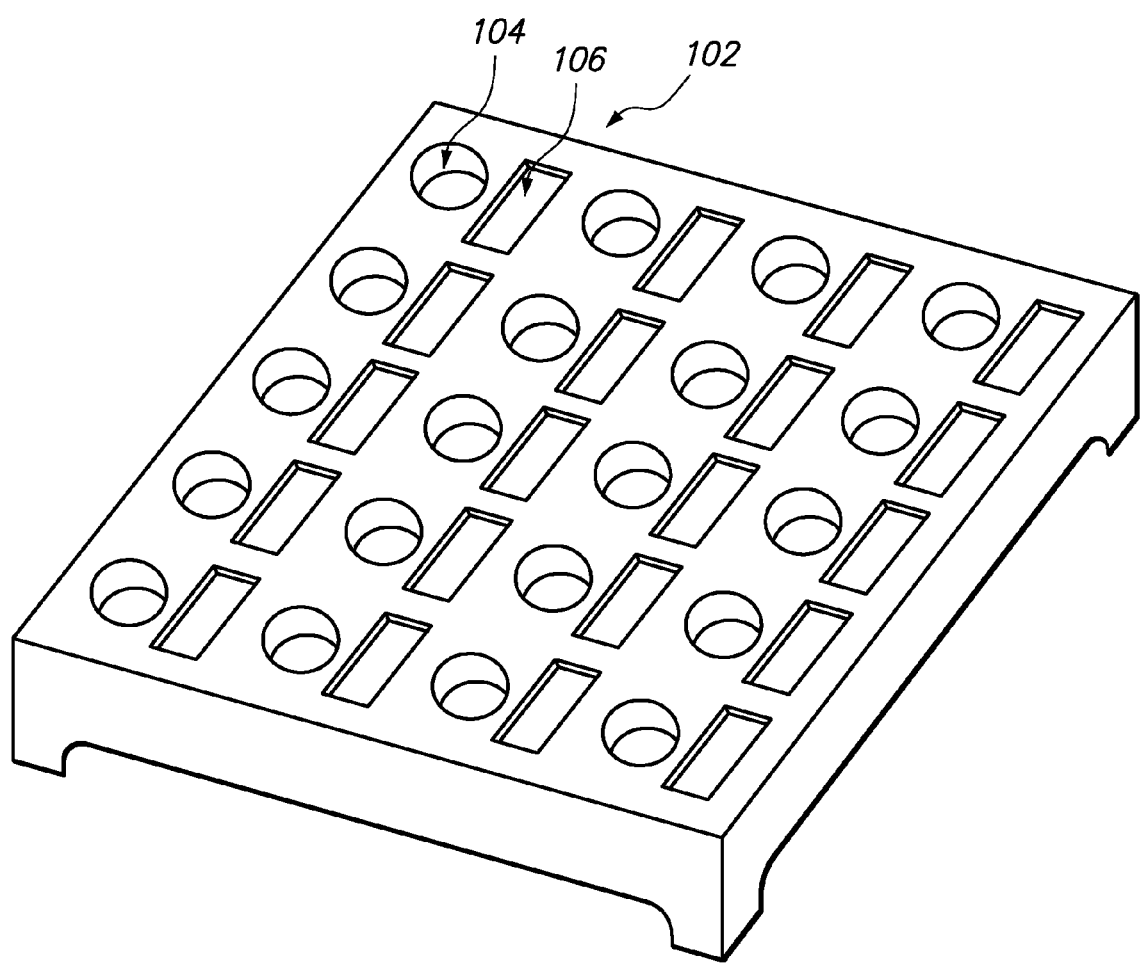
FIG. 3 depicts another embodiment of the carrier of the present invention, having slide locations directly adjacent to vial locations.

For example, FIG. 3 shows another configuration of the locations on the carrier 102. In this embodiment, the slide locations 106 are located directly adjacent to the vial locations 104. In some of these embodiments, the carrier 102 does not feature the walls and troughs that were featured in the embodiments shown in FIGS. 1 and 2.

In some embodiments, not shown in the figures, each location 106 features at least one indentation in at least one of its sides as finger access for easy removal of the slide 206 by the user. Other embodiments of the carrier 102 do not feature the finger access.

In some embodiments, the vial 204 is configured to hold a biological sample. Thus, the vial 204 comprises a container and a lid, where medical personnel obtain the biological sample and put in the vial 204, cap it with the lid, and send it to a laboratory for further processing. The biological sample can be a sample obtained during a cervical examination, urine, blood, saliva, stool, or other tissue.

In some embodiments, such as the one shown in FIGS. 1 and 2, the vial 204 sits within the location 104 such that the cap of vial 204 stays above the top surface of the trough 108. In embodiments, such as the one shown in FIG. 3, the vial 204 sits within the location 104 such that the cap of vial 204 stays above the top surface of the carrier 102. In other embodiments, the vial 204, including its cap, sink within the carrier 102 such that no portion of the vial 204 raises above the top surface of the carrier 102 or the trough 108. In some of these embodiments, the carrier 102 comprises means for removing the vial 204, such as depressions on the top surface of the carrier 102 or trough 108 where a mechanical arm, or the like, can reach the vial cap and pull the vial 204 out of the locations 104, or the location 104 has an open bottom where a mechanical arm, or the like, can push the vial 204 up and out of the location 104. In further embodiments, each location 104 features at least one indentation for finger access for easy removal of the vial 204 by the user.

In some aspects, the carrier disclosed herein is used to provide a one-to-one relationship between a biological sample and a prepared slide. In some embodiments, the automated processor, such as the ThinPrep® TP2000 device, is employed to process a number of biological samples. The user must keep track of the vials and the corresponding slides throughout the entire process. Currently, the user tries to keep the vials and the slides in close proximity to each other. However, if less than diligent care is used, or if the samples are somehow disturb by accident, it is difficult to determine which slide is smeared with the biological sample of which vial. Even if the vials and the slides are labeled properly, the disturbance causes undue time to be spent to re-establish the one-to-one correspondence between the vials and the misplaced slides.

The carriers disclosed herein have the added advantage that they keep one slide in close proximity to one vial, each having a defined location on the carrier. The close proximity of the locations on the carrier minimizes the chances of misplacing a slide with respect to its corresponding vial.

Thus, in another aspect, disclosed herein is a method of processing a plurality of biological samples in an automated processor, comprising:

obtaining a carrier comprising:
  a plurality of locations each configured to hold a vial, and a plurality of locations each configured to hold a slide, wherein there are as many of the slide locations as there are vial locations;
  a plurality of vials each containing a biological sample, each of the vials located in one of the plurality of vial locations; and
  a plurality of slides, each slide located in one of the plurality of slide locations;
 removing one of the vials from a location on the carrier;
 placing the removed vial within the automated processor;
 removing one of the slides from a location on the carrier;
 placing the removed slide within the automated processor;
 attaching a filter to an aspirator within the automated processor, the filter comprising a membrane;
 adhering a plurality of cells of the biological sample of the removed vial to the membrane of the filter;
 transferring the plurality of cells to the removed slide; and
 replacing the removed vial and the removed slide in the carrier.

In some embodiments, the above method further comprises marking each of the vials with at least one unique identifier.

In some embodiments, each of the slide locations in the above method is directly adjacent to one of the vial locations. In some of these embodiments, the location of the removed slide is directly adjacent to the location of the removed vial. In further embodiments, the methods disclosed herein further comprise marking the slide in the location directly adjacent to the vial with a unique identifier identical to the unique identifier of the vial.

In other embodiments, each of the slide locations is superimposed on one of the vial locations. In some of these embodiments, the location of the removed slide is superimposed on the location of the removed vial. Some of these embodiments further comprise removing one of the slides prior to removing one of the vials. In some of these embodiments, the methods disclosed herein further comprise marking the slide in the location superimposed on the vial with a unique identifier identical to the unique identifier of the vial.

It is understood by those of skilled in the art that the steps in the above method can be practiced in various different orders, and not all step need necessarily be performed. The listing of the steps in the order described above is but way of example and the steps of the method make be performed in different orders.

The invention may be embodied in other specific forms besides and beyond those described herein. The foregoing embodiments are therefore to be considered in all respects illustrative rather than limiting, and the scope of the invention is defined only by the appended claims and their equivalents, rather than by the foregoing description.

The invention claimed is:

1. A carrier for holding a biological sample vial and a slide for processing, the carrier comprising a plurality of first locations, each configured to hold a vial; and a plurality of second locations, each configured to hold only one slide, wherein each second location is adjacent to one of the first locations, and wherein each of the second locations is superimposed on a respective first location.

2. The carrier of claim 1, further comprising at least one finger access indentation at each second location.

3. The carrier of claim 1, further comprising at least one finger access indentation at each first location.

4. The carrier of claim 1, the vial having a cap, the first locations each having a depth such that the vial cap is positioned below a surface of the carrier when a vial is positioned therein.

5. The carrier of claim 1, further comprising a trough, wherein each of the first locations is located in the trough.

6. The carrier of claim 5, the vial having a cap, and wherein the first locations have a depth such that the vial cap is positioned above a surface of the trough when a vial is positioned therein.

7. The carrier of claim 5, the vial having a cap, and wherein the first locations have a depth such that the vial cap is positioned below a surface of the trough when a vial is positioned therein.

8. A carrier for holding a biological sample vial and a slide for processing, the carrier comprising
   a plurality of first locations, each configured to hold a vial;
   a plurality of second locations, each configured to hold only one slide; and
   a trough, wherein each of the first locations is located in the trough,
   wherein each second location is adjacent to one of the first locations, and
   wherein each of the second locations is superimposed on a respective first location such that, when the slide is placed in one of the second locations, the slide bridges the trough.

9. A carrier for holding a biological sample vial and a slide for processing, the carrier comprising
   a plurality of first locations, each configured to hold a vial; and
   a plurality of second locations, each configured to hold only one slide,
   wherein each second location is adjacent to one of the first locations, and
   wherein the first and second locations are configured such that slides placed in the second locations are positioned directly above vials placed in the first locations.

* * * * *